United States Patent [19]

Kingsman et al.

[11] Patent Number: 4,898,823
[45] Date of Patent: Feb. 6, 1990

[54] DNA SEQUENCE

[75] Inventors: Alan J. Kingsman; Susan M. Kingsman, both of Islip, England

[73] Assignee: Celltech Limited, Sough, England

[21] Appl. No.: 165,388

[22] Filed: Feb. 29, 1988

Related U.S. Application Data

[63] Continuation of Ser. No. 697,584, filed as PCT GB84/00189 on May 31, 1984, published as WO84/04757 on Dec. 6, 1984, abandoned.

[30] Foreign Application Priority Data

May 31, 1983 [GB] United Kingdom ............... 8314961

[51] Int. Cl.$^4$ .................. C12N 15/00; C12N 1/20; C12N 5/00
[52] U.S. Cl. ............................. 435/172.3; 435/69.1; 435/320; 435/255; 435/256; 536/27; 935/28; 935/37; 935/69
[58] Field of Search ............... 435/68, 70, 91, 172.3, 435/255, 256, 320; 935/28, 37, 69; 536/27

[56] References Cited

PUBLICATIONS

Efficient Expression of the Saccharomyces Cerevisiae PGK Gene Depends on an Upstream Activation Sequence but Does Not Require TATA Sequences, Ogden et al., Molecular and Cellular Biology, Dec. 1986, pp. 4335-4343.
Nucleic Acids Research, vol. 15, No. 17, 1987, Stanway et al., pp. 6855-6873.

*Primary Examiner*—Robin Teskin
*Attorney, Agent, or Firm*—Cushman, Darby & Cushman

[57] ABSTRACT

An upstream activator sequence derived from the yeast PGK gene. The upstream activator sequence is contained in the 5' region of the yeast PGK gene between nucleotides -324 and -455. The upstream activator sequence has synthetic linkers attached to either end to facilitate attachment to a vector. Vectors including the upstream activator sequence and a heterologous promoter sequence are described. The upstream activator sequence is used in a method for increasing the expression level of a yeast expression vector.

5 Claims, 5 Drawing Sheets

```
-820
*
  TCGATTAATT TTTTTTTCTT TCCTCTTTTT ATTAACCTTA ATTTTTATTT

-770
*
  TAGATTCCTG ACTTCAACTC AAGACGCACA GATATTATAA CATCTGCATA

-720
*
  ATAGGCATTT GCAAGAATTA CTCGTGAGTA AGGAAAGAGT GAGGAACTAT

-670
*
  CGCATACCTG CATTTAAAGA TGCCGATTTG GGCGCGAATC CTTTATTTTG

-620
*
  GCTTCACCCT CATACTATTA TCAGGGCCAG AAAAAGGAAG TGTTTCCCTC

-570
*
  CTTCTTGAAT TGATGTTACC CTCATAAAGC ACGTGGCCTC TTATCGAGAA

-520
*
  AGAAATTACC GTCGCTCGTG ATTTGTTTGC AAAAAGAACA AATGAAAAAC

-470          pMA339
*
  CCAGACAGCG CTCGACTTCC TGTCTTCCTA TTGATTGCAG CTTCCAATTT

-420
*
  CGTCACACAA CAAGGTCCTA GCGACGGCTC ACAGGTTTTG TAACAAGCAA

-370                                              pMA337
*
  TCGAAGGTTC TGGAATGGCG GGAAAGGGTT TAGTACCACA TGCTATGATG

-320                                Pvu I
*
  CCCACTGTGA TCTCCAGAGC AAAGTTCGTT CGATCGTACT GTTACTCTCT

-270
*
  CTCTTTCAAA CAGAATTGTC CGAATCGTGT GACAACAACA GCCTGTTCTC
```

FIG. 3

```
-220
  *
   ACACACTCTT TTCTTCTAAC CAAGGGGGTG GTTTAGTTTA GTAGAACCTC

-170
  *
   GTGAAACTTA CATTTACATA TATATAAACT TGCATAAATT GGTCAATGCA

-120
  *
   AGAAATACAT ATTTGGTCTT TTCTAATTCG TAGTTTTTCA AGTTCTTAGA

-70
  *
   TGCTTTCTTT TTCTCTTTTT TACAGATCAT CAAGAAGTAA TTATCTACTT
                                    ┠────────────────▶
                                            RNA
-20
  *
   TTTACAACAA ATATAAAACA ATG TCT TTA TCT TCA AAG TTG TCT GTC CAA
                         MET SER LEU SER SER LYS LEU SER VAL GLN

30
  *
   GAT TTG GAC TTG AAG GAC AAG CGT GTC TTC ATC AGA GTT GAC TTC AAC GTC
   ASP LEU ASP LEU LYS ASP LYS ARG VAL PHE ILE ARG VAL ASP PHE ASN VAL 81                       pMA213
  *
   CCA TTG GAC GGT AAG AAG ATC│ACT TCT AAC CAA AGA ATT GTT GCT GCT TTG
   PRO LEU ASP GLY LYS LYS ILE│THR SER ASN GLN ARG ILE VAL ALA ALA LEU

132
  *
   CCA ACC ATC AAG TAC GTT TTG GAA CAC CAC CCA AGA TAC GTT GTC TTG GCT
   PRO THR ILE LYS TYR VAL LEU GLU HIS HIS PRO ARG TYR VAL VAL LEU ALA

183
  *
   TCT CAC TTG GGT AGA CCA AAC GGT GAA AGA AAC GAA AAA TAC TCT TTG GCT
   SER HIS LEU GLY ARG PRO ASN GLY GLU ARG ASN GLU LYS TYR SER LEU ALA

234
  *
   CCA GTT GCT AAG GAA TTG CAA TCA TTG TTG GGT AAG GAT GTC ACC TTC TTG
   PRO VAL ALA LYS GLU LEU GLN SER LEU LEU GLY LYS ASP VAL THR PHE LEU

285
  *
   AAC GAC TGT GTC GGT CCA GAA GTT GAA GCC GCT GTC AAG GCT TCT GCC CCA
   ASN ASP CYS VAL GLY PRO GLU VAL GLU ALA ALA VAL LYS ALA SER ALA PRO

336
  *
   GGT TCC GTT ATT TTG TTG GAA AAC TTG CGT TAC CAC ATC GAA GAA GAA GGT
   GLY SER VAL ILE LEU LEU GLU ASN LEU ARG TYR HIS ILE GLU GLU GLU GLY
```

FIG. 4

DNA SEQUENCE

This is a continuation of application Ser. No. 697,584, filed as PCT GB84/00189 on May 31, 1984, published as WO84/04757 on Dec. 6, 1984, which was abandoned upon the filing hereof.

The present invention relates to a DNA sequence. In particular it relates to an upstream activator sequence of the yeast phosphoglycerate kinase (PGK) gene, a vector containing the upstream activator sequence and a method for increasing the expression level from a yeast vector using the upstream activator sequence.

The recent advances in recombinaot DNA technology have been such that there are now many examples of the expression of heterologous gene products by host organisms. The commercial viability of such products is limited by the level of gene expression and there has been much research effort directed towards increasing expression levels.

In our copending European patent application EP-A2-0073635 we describe a number of plasmid vectors suitable for the expression of genetic material in yeasts. A particular vector described uses the promoter of the yeast PGK gene and is useful for the synthesis of commercially important polypeptides in yeast. The yeast PGK gene is itself expressed efficiently by a yeast cell and indeed the PGK promoter directs efficiently the expression of heterologous genetic material.

The analysis of the 5' region of other yeast genes e.g. CYC1 and HIS3 has lead to the discovery of sequences of DNA capable of potentiating the efficiency of promoter sequences of yeast genes. These sequences are known as upstream activator sequences (Faye et al. 1981 PNAS 78 2258; Lowry et al. 1983 PNAS 80, 151; Struhl 1982 PNAS 79, 7385). However all the genes analysed to date are expressed at low levels in yeast and consequently their promoter regions are of limited use for the construction of yeast vectors that direct the high level production of heterologous gene products.

Prior to the present invention it was not known whether efficiently expressed genes such as PGK contained upstream activator sequences and indeed, if such sequences did exist, whether they are primarily responsible for the efficiency of the expression of genes encoding abundant products. Furthermore if an upstream activator sequence from an efficiently expressed gene could be isolated it was not known whether it would function in a similar way to the 'Potentiator' sequences of higher organisms which are capable of activiating heterologous promoters (Wasylyk et al. 1983 Cell 32, 503).

According to the present invention we provide an upstream activator sequence derived from the yeast PGK gene. The upstream activator sequence is contained in the 5' region of the yeast PGK gene between nucleotides -324 and -456. The upstream activator sequence may be used in a DNA "cassette" to activate any yeast promoter. In such an application the upstream activator sequence may have synthetic linker sequences attached at either end to facilitate attachment to a vector.

Further according to the present invention we provide a yeast expression vector including the upstream activator sequence of the yeast PGK gene. Preferably the yeast expression vector contains a promoter sequence heterologous to the PGK gene.

Further according to the present invention we provide a method for increasing the expression level of a yeast expression vector comprising inserting the upstream activator sequence of the yeast PGK gene into the vector, upstream of a heterologous promoter sequence in the vector.

The heterologous promoter sequence may be any promoter sequence known to the art other than the PGK promoter sequence. For example, the promoter may be derived from the TRP1, ADH1, URA3, HIS3, or CYC1 gene sequences.

The invention is now illustrated by the following Example, with reference to the accompanying drawings in which.

Figure 5:
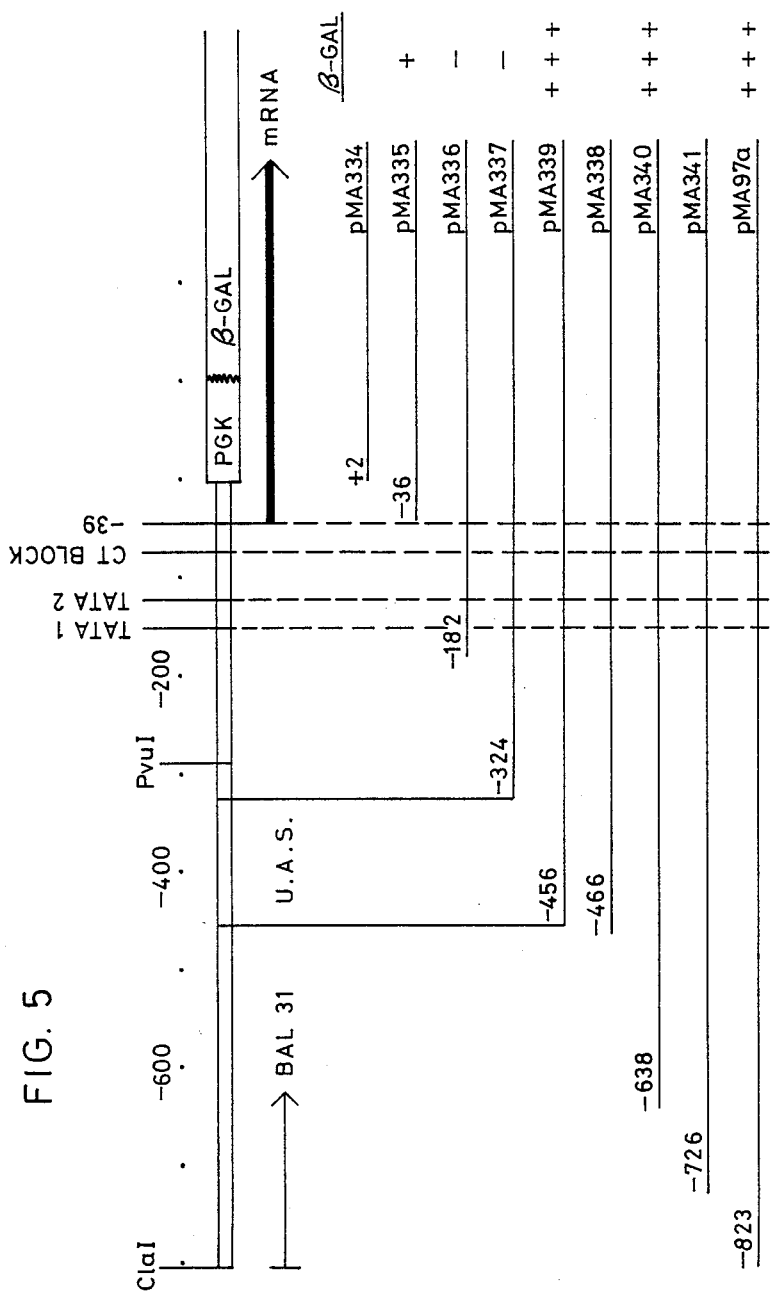

FIG. 3 shows the nucleotide sequence of a portion of the 5' region of the yeast PGK gene from necleotide -820 to nucleotide -220 inclusive, FIG. 4 shows the nucleotide sequence and amino acid sequence about the pM22a deletion end point, FIG. 5 shows a subjective estimate of the blue colour caused by $\beta$-galactosidase activity of yeasts transformed with plasmids pMA335, 336, 337, 339, 340 and 97a.

EXAMPLE

Use of the restriction enzymes, Bal 31 and general techniques were as described in European patent application EP-A2-0073635. $\beta$-galactosidase activity was assessed on XG plates (Rose et al.; 1981 PNAS 78, 2460). Yeast cell extracts were prepared following growth in SC-leucine medium (Hawthorne and Mortimer, 1960 Genetics 45, 1085). Cells were harvested in mid logarithmic growth and then disrupted as described in Rose et al. (1981 op. cit). Protein was measured using the method of Bradford (1976 Anal. Biochem. 72, 248) and reagents were supplied by Biorad. $\beta$-galactosidase was measured according to Miller (1972 Experiments in Molecular Genetics, Cold Spring Harbor Laboratory, N.Y.).

Figure 1:
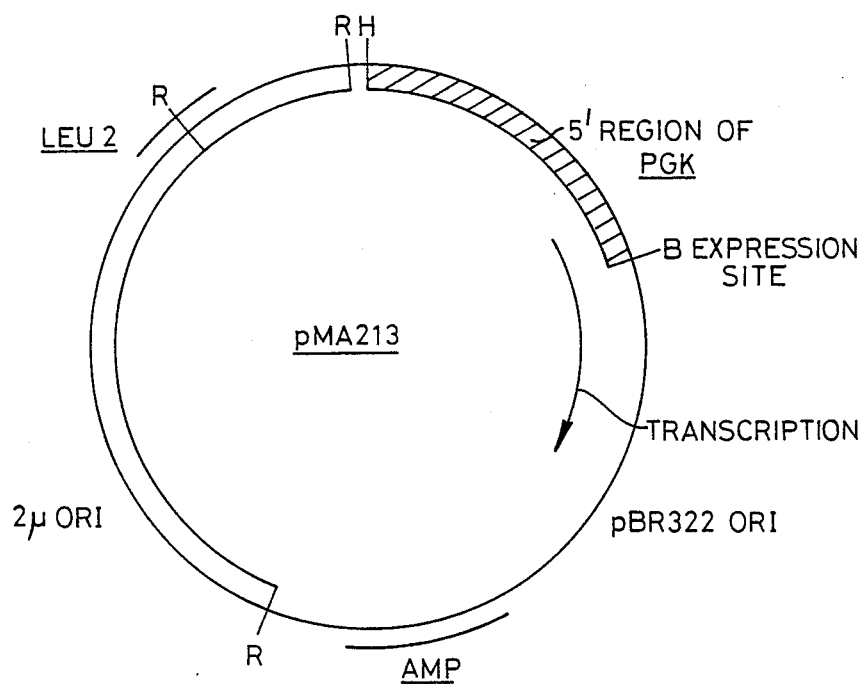
FIG. 1 is a schematic diagram of plasmid pMA213.

The starting molecule for the analysis of the 5' region of the yeast PGK gene was pMA213 (FIG. 1). Plasmid pMA213 is a member of the pMA22a deletion series described in European patent application EP-A2-0073635. The deletion endpoint of pMA 213 is such that when a 3.1 Kb Bam HI fragment containing the E. coli lacZ is inserted at the Bam HI expression site a PGK-$\beta$-galactosidase fusion protein is produced under the control of the PGK 'promoter'. This fusion protein has $\beta$-galactosidase activity and yeast (Saccharomyces cerevisiae) does not normally possess this enzyme activity. Yeast transformants containing this plasmid with the lacZ gene inserted give dark blue colonies on XG plates whereas the untransformed strain is white.

Figure 2:
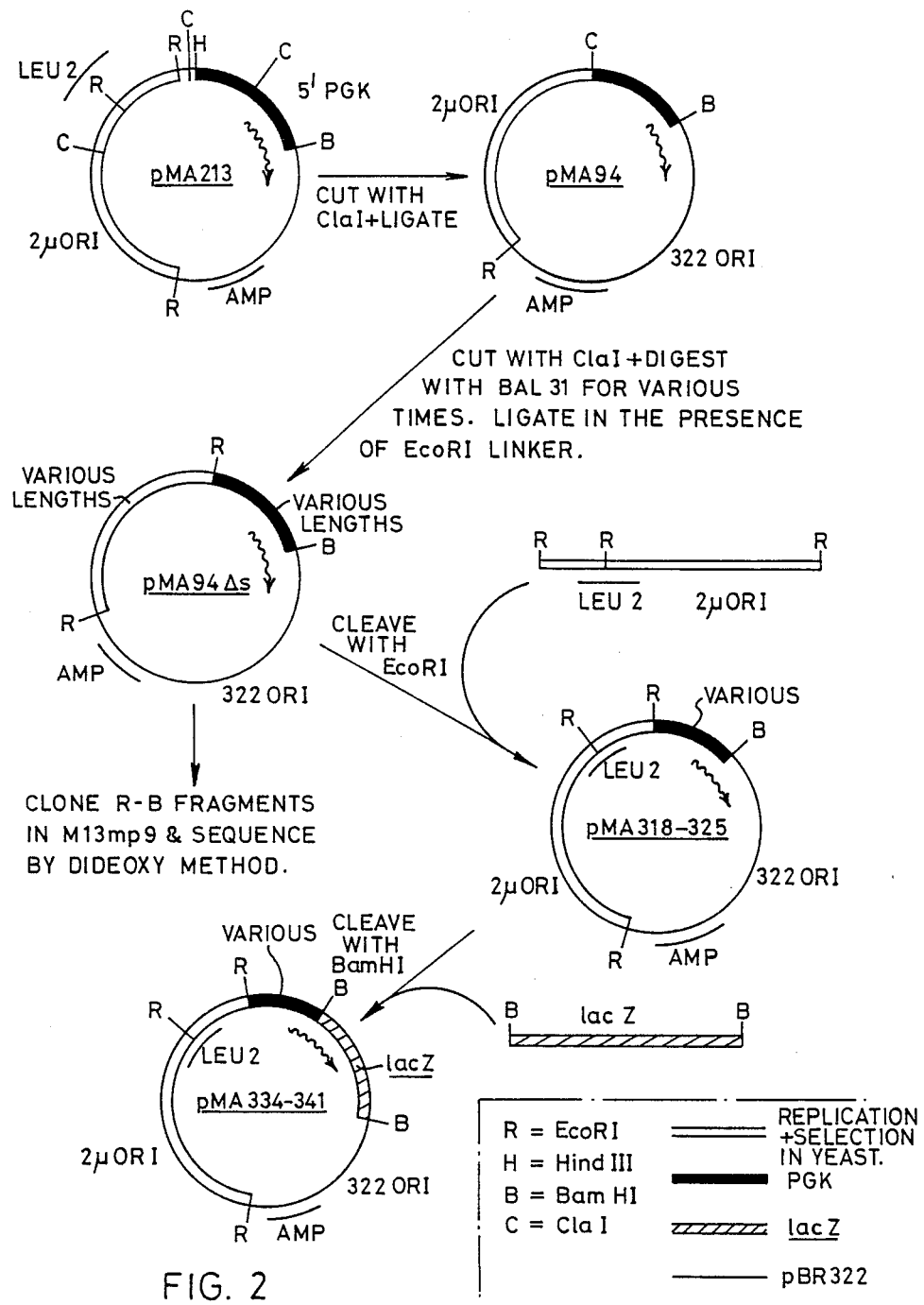
FIG. 2 is a schematic diagram of the construction of plasmids pMA318-325.

In order to generate a set of deletions which lacked various amounts of the 5' region of the PGK gene and in order to determine the nucleotide sequence from -220 to -820 the following constructions were performed (FIG. 2). Plasmid pMA 213 was cleaved with Cla I and then ligated to remove the two smaller Cla I fragments from pMA 213 to form plasmid pMA94. Plasmid pMA94 was then cleaved with Cla I and then digested for various times with exonuclease Bal 31. The resulting pool of deleted molecules was then ligated in the presence of Eco RI linkers (GGAATTCC) and then used to transform E. coli strain ADEC28 (European Patent application EP-A2-0073635) to leucine independence and ampicillin resistance. Colonies were screened for plasmids with two Eco RI sites and classified on the basis of the length of the smaller Eco RI - Bam HI fragemnt. This collection of plasmids is known as the pMA 94 deletion series. Eight of these were selected to give an even distribution of end points across the 5' region of the PGK gene. Each of these was cleaved with Eco RI and ligated with the 2μ:LEU2 yeast selection and replication module (European patent application EP-A2-0073635) resulting in a series of molecules, pMA318–325, which are capable of replication in yeast and which contain various amounts of the 5' region of the PGK gene. Each of these derivatives was then cleaved with Bam HI and ligated in the presence of the 3.1 Kb Bam HI fragment from plasmid pMC1871 (constructed by Dr. M. Casadaban) bearing the E. coli β-galactosidase (lacZ) gene. Plasmids containing the lacZ gene inserted into the Bam HI site in the correct orientation were selected and formed the set of eight plasmids pMA 334–341. In addition the small Eco RI - Bam HI fragments from the selected eight members of the pMA94 deletion series were inserted into Eco RI and Bam HI cleaved M13mp8 (Messing and Vieira. 1983 Gene 19, 269) and sequenced by the dideoxy procedure (Sanger et al. 1977 PNAS 74, 5463). This generated overlapping sequence data from -820 to -220 and defined exactly the end points of the selected pMA94 deletions. The sequence data is shown in FIG. 3 and the pMA22a deletion end point in pMA 213 is shown in FIG. 4. The organisation of the 5'-PGK-lacZ fusions in plasmids pMA334–341 and the positions ok the deletion end points are shown in FIG. 5.

In order to assay the expression capabilities of these deleted 5' regions we transformed yeast strain MD40-4C (European patent application EP-A2-0073635) with plasmids pMA335, 336, 337, 339, 340 and 97a (FIG. 5) and then plated these transformants onto XG plates. FIG. 5 gives a subjective estimate of the intensity of blue colour in the colonies and therefore of -galactosidase activity. These estimates were confirmed by precise quantitation of β-galactosidase activity in extracts of the transformants (Table 1).

TABLE 1

| β-Galactosidase Activities in Extracts of MD40-4C Transformed with Various Plasmids | |
|---|---|
| Plasmid | β-galactosidase activity |
| pMA335-36 | 143 |
| pMA336-182 | 12.5 |
| pMA337-324 | 12.5 |
| pMA339-456 | 4266 |
| pMA97a-823 | 3309 |

Activities are expressed as nmol o-nitrophenol/min/mg protein.

These data clearly demonstrate the presence of an upstream activator sequence between positions -324 and -456 in the 5' region of the yeast PGK. This is the first demonstration of such a sequence in an efficiently expressed yeast gene. This sequence is underlined in the nucleotide sequence (-820 to -220) given in FIG. 3. The upstream activator sequence is responsible for at least a 300-fold stimulation of expression and is therefore essential for the efficient function of the PGK 'promoter' and any expression vectors dependent on the PGK expression signals.

It will of course be understood that the present invention has been described above purely by way of example, and modifications of detail can be made within the scope and spirit of the invention.

We claim:

1. An isolated upstream activator sequence (UAS) derived from the Saccharomyces phosphoglycerate kinase (PGK) gene which is contained in the 5' region of the PGK gene between nucleotides -324 and -456, which UAS when inserted upstream of a yeast promotor is capable of potentiating the efficiency thereof.

2. An upstream activator sequence according to claim 1 having synthetic linker sequences attached to either end to facilitate attachment to a vector.

3. A yeast expression vector which comprises the isolated upstream activator sequence of claim 1 operably linked to a yeast promoter other than the Saccharomyces PGK promoter.

4. A method for increasing the efficiency of a yeast promotor, other than the Saccharomyces phosphoglycerate Kinase (PGK) promoter which comprises inserting the upstream activator sequence of claim 1 upstream of said yeast promoter thereby resulting in a hybrid promoter with enhanced efficiency.

5. The method of claim 4 wherein the promoter is selected from the group consisting of TRP1, ADH1, URA3, HIS3, and CYC1 gene sequences.

* * * * *